United States Patent
Tan et al.

(10) Patent No.: US 7,495,106 B1
(45) Date of Patent: *Feb. 24, 2009

(54) O-AMINOPHENOL-CONTAINING AB-MONOMER FOR HETEROCYCLIC RIGID-ROD POLYMERS

(75) Inventors: Loon-Seng Tan, Centerville, OH (US); Ramamurthi Kannan, Cincinnati, OH (US); Jim C. Spain, Atlanta, GA (US); Lloyd J. Nadeau, Mexico Beach, FL (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/998,862

(22) Filed: Nov. 29, 2007

Related U.S. Application Data

(60) Provisional application No. 60/877,020, filed on Dec. 4, 2006.

(51) Int. Cl.
C07D 277/66 (2006.01)
(52) U.S. Cl. .................. 548/178; 435/252.8; 435/25
(58) Field of Classification Search .................. None
See application file for complete search history.

(56) References Cited

U.S. PATENT DOCUMENTS 7,364,881 B1 * 4/2008 Nadeau et al. ............. 435/128

FOREIGN PATENT DOCUMENTS

WO  WO 2007032296 A1 * 3/2007

OTHER PUBLICATIONS

Kadiyala et al. Construction of *Escherichia coli* Strains for Conversion of Nitroacetophenones to ortho-Aminophenols., Appl. Environ. Microbiol., Nov. 2003, (69), p. 6520-6526.*

X. Hu et al., "Rigid-Rod Polymers: Synthesis, Processing, Simulation, Structure and Properties", 2003, *Macromol. Mater. Eng.*, 288, No. 11, pp. 823-843.

R.C. Evers et al., "Articulated All-Para Polymers with 2,6-Benzobisoxazole, 2,6-Benzobisthiazole, and 2,6-Benzobisimidazole Units in the Backbone", 1981, *Macromolecules*, 14, pp. 925-930.

S. Kumar et al, "Synthesis, Structure, and Properties of PBO/SWNT Composites", 2002, *Macromolecules*, 35, pp. 9039-9043.

Y. So, "The Effect of Limited Monomer Solubility in Heterogeneous Step-Growth Polymerization", 2001, *Acc. Chem. Res.*, 34, pp. 753-758.

S. Jenekhe et al, "Photoinduced Electron Transfer in Binary Blends of Conjugated Polymers", 1996, *Chem. Mater.*, vol. 8, No. 10, pp. 2401-2404.

S. Jenekhe et al., "Nonlinear Optical Properties of Poly(p-phenylenebenzobisoxazole", 1992, *Chem. Mater.* 4, pp. 683-687.

S. Park et al., "Structure of poly(p-phenylenebenzobisoxazole) (PBZO) and poly (p-henylenebenzobisthia-zole) (PZBT) for Proton Exchange Membranes (PEMs) in Fuel Cells", 2004, *Polymer* 45, pp. 49-59.

L.J. Nadeau et al., "Conversion of 2-(4-carboxyphenyl)-6-nitrobenzothiazole to 4-(6-amino-5-hydroxybenzo-thiazol-2-yl)benzoic Acid by a Recombinant *E. coli* Strain", *Chem. Commun*, pp. 564-565.

L.J. Nadeau et al., "Bacterial Conversion of Hdyroxylamino Aromatic Compounds by boty Lyase and Mutase Enzymes Involves Intramolecular Transfer of Hydroxyl Groups", May 2003, *Appl. Environ. Microbiol.*, vol. 69, No. 5, pp. 2786-2973.

V. Kadiyala et al., "Construction of *Escherichia coli* Strains for Conversion of Nitroacetophenones to ortho-Aminophenols ", Nov. 2003, *Appl. Environ. Microbiol.*, vol. 69, No. 11, pp. 6520-6526.

L.J. Nadeau et al., Production of 2-amino-5-phenoxyphenol from 4-nitrobiphenyl Ether Using Nitrobenzene Nitroreductase and Hydroxylaminobenzene Mutase from *Pseudomonas pseudoalcaligenes* JS45, 2000, Journal of Industrial Microbiology & Biotechnology, vol. 24, pp. 301-305.

* cited by examiner

*Primary Examiner*—Kamal A Saeed
*Assistant Examiner*—Valerie Rodriguez-Garcia
(74) *Attorney, Agent, or Firm*—AFMCLO/Jaz; Bart S. Hersko

(57) ABSTRACT

A novel o-aminophenol-carboxylic AB-monomer with the following chemical structure:

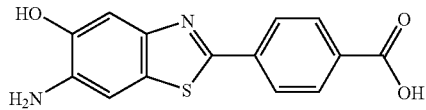

for synthesizing new rigid-rod polybenzobisazoles was prepared from the corresponding nitrobenzothiazolecarboxylic acid via an enzymatic process.

3 Claims, No Drawings

O-AMINOPHENOL-CONTAINING AB-MONOMER FOR HETEROCYCLIC RIGID-ROD POLYMERS

CROSS REFERENCE TO RELATED APPLICATION

This application claims priority benefit of U.S. Provisional Application No. 60/877,020 filed on Dec. 4, 2006.

RIGHTS OF THE GOVERNMENT

The invention described herein may be manufactured and used by or for the Government of the United States for all governmental purposes without the payment of any royalty.

BACKGROUND OF THE INVENTION

The present invention relates to heterocyclic monomers, particularly to o-amino-hydroxy-benzothiazole-benzoic acid and a new enzymatic process to synthesize it from the corresponding nitro-benzothiazole-benzoic acid compound.

4,6-Diaminoresorcinol and 2,5-diamino-1,4-benzenedithiol (usually stored as dihydrochloride salts) are key co-monomers for the synthesis of high-strength-high-modulus, thermally resistant rigid-rod poly(p-phenylenebenzobisoxazole) (PBO) and poly(p-phenylenebenzobisthiazole (PBT) polymers for lightweight structural, nonlinear optical and electronic applications.

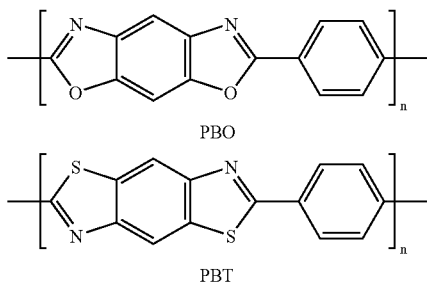

PBO

PBT

More recently, PBO and PBT have been considered for use in the proton-exchange membranes of fuel cells. While an AB-monomer 4-[5-amino-6-hydroxybenzoxazol-2-yl]benzoic acid has been prepared and utilized in the synthesis of the correspond PBO polymer, the analogous AB-monomer for PBT, namely, 4-[5-amino-6-mercaptobenzothiazol-2-yl]benzoic acid is yet to be synthesized. In addition to having an intrinsically perfect stoichiometry that helps to promote high molecular weight polymers in polycondensation processes, AB-monomers are also useful starting materials for the synthesis of AB diblock copolymers, ABA triblock copolymers and star polymers. They can also be grafted onto appropriately functionalized surfaces. The availability of the above aminophenol derivative is limited because the synthesis is complex and yields are low. Recent advances in biologically converting aromatic nitro compounds to the corresponding o-aminophenols suggest the possibility of synthesizing novel AB-monomers such as 4-(6-amino-5-hydroxybenzothiazol-2-yl)benzoic acid, and in principle, the corresponding rigid-rod polymer that is a hybrid of both PBO and PBT with respect to the chemical structure.

Accordingly, it is an object of the present invention to provide a process for the preparation of the 4-(6-amino-5-hydroxybenzothiazol-2-yl)benzoic acid.

Although the requisite starting nitro compounds (either as a carboxylic acid, viz. 2-(4-carboxyphenyl)-6-nitrobenzothiazole, or an ethylester, viz. 2-(4-carboethoxyphenyl)-6-nitrobenzothiazole) are relatively simple molecules, they have not been reported in open or patent literature. Thus, it is another object of this invention to provide the following nitrobenzothiazolecarboxylic acid.

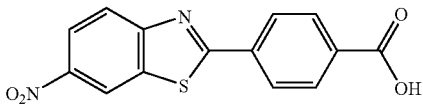

The simple route to the subject nitrobenzothiazolecarboxylic acid is via direct nitration of 2(4-carboxyphenyl)benzothiazole, which can be synthesized from the condensation reaction between 2-aminothiophenol and 4-carboxybenzaldehyde in hot dimethyl sulfoxide. However, the poor solubility of 2(4-carboxyphenyl)benzothiazole and 2-(4-carboxyphenyl)-6-nitrobenzothiazole has necessitated additional esterification/de-esterification steps in order to rigorously establish the identity and purity of the subject AB-monomer.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided a new o-aminophenol-containing, benzothiazolecarboxylic-acid AB-monomer formed by converting via an enzymatic process from the corresponding nitrobenzothiazole-carboxylic acid.

DETAILED DESCRIPTION OF THE INVENTION

In a prior art, it has been demonstrated that nitroarenes are converted to o-aminophenols by nitroreductase and mutase enzymes as described in the following reports: (a) S. F. Nishino and J. C. Spain, *Appl. Environ. Microbiol.*, 1993, 59, 2520. A. Schenzle, H. Lenke, P. Fischer, P. A. Williams, and H.-J. Knackmuss, *Appl. Environ. Microbiol.*, 1997, 63, 1421. H. -S; (b) Park and H. -S. Kim, *J. Bacteriol.*, 2000, 182, 573. Y. Hasegawa, T. Muraki, T. Tokuyama, H. Iwaki, M. Tatsuno, and P. C. K. Lau, *FEMS Microbiol. Letters*, 2000, 190, 185; (c) T. Spiess, F. Desiere, P. Fischer, J. C. Spain, H. -J. Knackmuss, and H. Lenke, *Appl. Environ. Microbiol.*, 1998, 64, 446. The nitroreductase reduces nitroaromatic compounds to hydroxylaminoarenes, as shown by (a) H. Nivinskas, R. L. Koder, Z. Anusevicius, J. Sarlauskas, A. -F. Miller, and N. Cenas, *Archives Biochemistry Biophyics*, 2001, 385, 170; (b) C. C. Somerville, S. F. Nishino, and J. C. Spain, *J. Bacteriol.*, 1995, 177, 3837, and hydroxylaminobenzane mutase catalyzes a regio-specific reaction converting hydroxylaminoarenes to the corresponding o-aminophenols by an intramolecular transfer of the hydroxyl group, as described in L. J. Nadeau, Z. He, and J. C. Spain, *Appl. Environ. Microbiol.*, 2003, 69, 2786. Furthermore, an *E. coli* containing nitroreductase and mutase converts simple nitroarenes regio-specifically to o-aminophenols at high yields, as shown in (a) V. Kadiyala, L. J. Nadeau, and J. C. Spain, *Appl. Environ. Micro-*

*biol.*, 2003. 69, 6520; (b) L. J. Nadeau, Z. He, and J. C. Spain, *J. Indust. Microbiol. Biotechnol.*, 2000, 24, 301.

The cells of *E. coli* C43(DE3)pNbzAHabA (i.e. strain JS995) were grown and induced as described in [4] Kadiyala, V., Nadeau, L. J., Spain, J. C. 2003. Construction of *Escherichia coli* strains for the conversion of nitroacetophenones to the ortho-aminophenol. Appl. Environ. Microbiol. 69:6520-6526. incorporated herein by reference. 2-(4-Carboxyphenyl)-6-nitrobenzothiazole 7a (49 µM) was incubated with the cells and HPLC analysis of the reaction mixture revealed a transformation rate for the parent compound of 0.9 nmoles $min^{-1}$ $mg^{-1}$ protein and the accumulation of one product (FIG. 1). Liquid chromatography-mass spectral (+APCI) analysis of the product revealed a 287 m/z as expected of an aminophenol. The conversion efficiency was 100%. The transformation was scaled up to a 2 L bioreactor containing M9 medium (30° C.), as described in J. Sambrook, E. F. Fritsch, and T. Maniatis, Molecular cloning: a laboratory manual, 2nd ed. Cold Spring Harbor Laboratory Press, Cold Spring Harbor, N.Y. 1989, supplemented with sorbitol (20 g/L), ampicillin (100 µg/L) and isopropylthio-β-D-galactoside (1 mM). Induced cells were added to the bioreactor ($A_{600}$=8.0) and 7a (5 mM) dissolved in $NH_4OH$ (2 N) at 65° C. was delivered repeatedly to the reactor. The disappearance of reactant and accumu-lation of product was monitored by HPLC. Over a 2 hour period, 200 mg of 7a was converted. The cells were removed by centrifugation and the product was precipitated by adjusting the pH of the supernatant to 2.7 with HCl. Green crystals were recovered by centrifugation. The crystals were dissolved in $NH_4OH$, filtered and recrystallized by lowering the pH to 2.7. The pelleted crystals were dried overnight under vacuum, washed with water and then acetone. The melting point was 326-328° C.

The proton NMR spectrum (270 MHz) of the purified compound in DMSO-$d_6$ showed that in the aromatic proton region, there were three singlet peaks at δ (ppm) 7.117, 7.309, and 8.012 at relative intensities of 1:1:4. The fact that only two distinct singlets (δ 7.117, 7.309 ppm) were observed from the two protons on the phenyl ring with tetra-substitution ruled out the isomeric structure 6 or mixture of 5 and 6 (FIG. 2). The Fourier-transformed infrared FT-IR (KBr) spectrum is consistent with the NMR data, indicating the presence of v(C=O) of carboxylic acid at 1692 $cm^{-1}$ and a strong, broad band centered ~3431 $cm^{-1}$ that is attributable to the hydroxyl-group vibrations of the carboxylic acid and the phenol moieties. The symmetrical and asymmetrical $NH_2$ stretches, typically detected as doublet at ~3400 and ~3500 $cm^{-1}$ respectively, are most likely hidden underneath the broad v(OH) band. Electron-impact mass spectroscopy gave a molecular ion with m/z=285.96 (100% relative abundance). Thus, all the available spectroscopic data confirm the structure of the product as 4-(6-amino-5-hydroxybenzothiazol-2) benzoic acid.

The biocatalyst, *E. coli* C43(DE3)pNbzAHabA converts 2-(4-carboxyphenyl)benzothiazole to a potentially useful o-aminophenolic synthon for the synthesis of novel polymers. Our previous work indicated that the combination of the reductase and mutase enzymes could catalyze the transformation of very simple nitroaromatic compounds to the corresponding ortho-aminophenols. The results presented here indicate that the biocatalyst can transform more complex and potentially useful nitroaromatic compounds stoichiometrically to the ortho-aminophenols. Such conversions using traditional organic chemistry would be prohibitively complex and expensive.

Applicants have made available to the public without restriction a deposit of *E. coli* Strain JS995 with the American Type Culture Collection (ATCC), 10801 University Blvd., Manassas, Va. 20110, U.S.A., ATCC Deposit No. PTA-8615. The date of the deposit was 23 Aug., 2007. The deposit with the ATCC was taken from the same deposit maintained by the Air Force, since prior to the filing date of this application. All restrictions imposed by the depositor on the availability to the public of the deposited material will be irrevocably removed upon the granting of the patent. The deposit of the *E. coli* Strain JS995 without restriction will be maintained at the ATCC Depository, which is a public depository, for a period of 30 years, or five years after the most recent request, or for the effective life of the patent, whichever is longer, and will be replaced if it becomes nonviable during that period.

The following Examples illustrate the invention:

EXAMPLE 1

2-(4-Carboxyphenyl)benzothiazole

A mixture of 2-aminothiophenol (9.00 ml, 0.08 mol), 4-carboxybenzaldehyde (10.1 g, 0.07 mol) and DMSO (40 mL) was heated to 145° C., and held at this temperature for 3.5 hours. The reaction mixture was diluted with water, and separated solids were collected, dried and recrystallized from acetic acid; 14.15 g, (82% yield), white solid, m.p. 294.1-295.5° C. Mass Spectrum: m/z, 255 ($M^+$), 238 (M—OH), 210 (M—COOH), 108. FT-IR (KBr; $cm^{-1}$): 3051 (br; OH), 1684 (CO), 1609, 1424, 1407, 1291, 970, 756. Anal. Calcd for $C_{14}H_9NO_2S$: C, 65.87; H, 3.55; N, 5.49; S, 12.56%. Found: C, 65.71; H, 3.96; N, 5.30; S, 12.66%. NMR: not available due to poor solubility.

EXAMPLE 2

2-(4-Carboethoxyphenyl)benzothiazole

To a slurry of 2-(4-carboxyphenyl)benzothiazole (4.5 g, 17 mmol.) in DMF (38 mL), potassium carbonate (5.39 g, 39 mmol) was added and the mixture was cooled in an ice bath. Bromoethane (7.2 mL, 102 mmol) was added in portions, and the mixture was allowed to come to room temperature. After 48 hours, the mixture was poured into water and the separated solids (4.51 g) were collected. A solution of the crude product was passed through a column of silica gel. The product residue (4.19 g), left after evaporation of the solvent, was recrystallized from ethanol; 3.96 g (81% yield), m.p. 132-133.6° C. Mass spec: m/z 283 ($M^+$). Anal. Calcd for $C_{16}H_{13}NO_2S$: C, 67.83; H, 4.62; N, 4.94; S, 11.31%. Found, C, 67.86; H, 4.62; N, 4.89; S, 11.45%. FT-IR (KBr; $cm^{-1}$): 3100 ($sp^2C$—H), 2989 ($sp^3C$—H), 1710 (C=O), 1522 (asym $NO_2$), 1341 (sym $NO_2$), 1279 (C—O—C), 1108, 773, 753, 696. $^1H$ NMR ($CDCl_3$; δ in ppm): 1.45 (t, 3H, methyl), 4.45 (q, 2H, $OCH_2$), 7.4-7.55 (m, 2 ArH), 7.9 (d, 1 ArH), 8.05-8.20 (m, 5 ArH). $^{13}C$ NMR ($CDCl_3$; δ in ppm): 14.76, 61.72 ($sp^3$ C), 122.12, 123.99, 126.09, 126.99, 127.78, 130.61, 132.79, 135.67, 137.67, 137.74, 154.51, 166.32 ($sp^2C$).

EXAMPLE 3

2-(4-Carboethoxyphenyl)-6-nitrobenzothiazole

To nitric acid (sp.gr. 1.49, 90%, 160 mL), 2-(4-carboxyphenyl)benzothiazole (16.0 g) was added in portions, the mixture was stirred at room temperature for 6 hour and poured onto crushed ice. The separated solids were collected, washed with water, and air-dried (17.99 g). The crude product was recrystallized twice from a mixture of toluene and ethanol (2:3), to get pure nitroester, 13.08 g (81% yield), m.p. 219-220° C. Mass spec: m/z 328 (M+). Anal. Calcd for $C_{16}H_{12}N_2O_4S$: C, 58.53; H, 3.68; N, 8.53; S, 9.77%. Found: C, 58.42; H, 3.71; N, 8.50; S, 9.78%. Mass spectrum: m/z, 328 (M+), 300 (M—$C_2H_4$), 283 (M—OEt), 237 (M—$NO_2$), 209(237—CO). IR ($cm^{-1}$): 3094 ($sp^2C$—H), 2987 (($sp^3C$—H)), 1710 (C=O), 1522 (asym. $NO_2$), 1340 (sym. $NO_2$), 1278 (C—O—C), 1108. $^1H$ NMR ($CDCl_3$; δ in ppm): 1.42, 1.44, 1.47 (t, 3H, methyl), 4.40, 4.42, 4.45, 4.48 (q, 2H, $OCH_2$), 8.16, 8.18 (d, 1H, peri ArH), 8.19 (s, 4 ArH), 8.37, 8.38, 8.40, 8.41 (d, d, 1 ArH), 8.86, 8.87 (d, 1 ArH). $^{13}C$ NMR ($CDCl_3$; δ in ppm): 14.40, 61.51 ($sp^3C$), 118.33, 122.10, 123.77, 127.80, 130.39, 133.50, 135.52, 136.27, 145.20, 157.66, 165.61, 172.32.

EXAMPLE 4

2-(4-Carboxyphenyl)-6-nitrobenzothiazole

A mixture of 2-(4-carboethoxyphenyl)-6-nitrobenzothiazole (8.0 g, 24 mmol), acetic acid (80 mL), and hydrobromic acid (48% in water, 80 mL) was kept at reflux (105° C.) for 8 hours and cooled. The slurry of product was filtered, and the solid was washed with water, and dried, 6.84 g. The crude product was reslurried in a mixture of acetic acid (100 mL), water (100 mL) and sodium acetate (10 g) for 2 hours. The recovered product was dried and slurried at room temperature in dichloromethane (100 mL). The product was then extracted in a Soxhlet with glacial acetic acid. The extract deposited pure nitro-acid, which was isolated in two crops totaling 5.35 g (74% yield). Both crops were dried at 210° C. under 0.3 mmHg for 3 hours. Crop-1 weighed 3.32 g, and had m.p. 352-355° C. Mass spec: m/z 300 (M+). Anal Calcd for $C_{14}H_8N_2O_4S$: C, 56.00; H, 2.69; N, 9.33; S, 10.68%. Found: C, 56.33; H, 2.44; N, 9.44; S, 11.06%. Crop-2 (2.03 g) had m.p. 352-356° C. Anal Found: C, 55.96; H, 2.69; N, 9.31; S, 10.68%. FT-IR (KBr; $cm^{-1}$): 3101 ($sp^2$—C—H), 1695 (C=O), 1517 (asym. $NO_2$), 1346 (sym. $NO_2$), 1293 (C—O—C), 784.

EXAMPLE 5

4-(6-Amino-5-hydroxybenzothiazol-2-yl)benzoic Acid

E. coli C43pNBzHabA carrying the recombinant plasmid was grown at 37° C. in 250 ml of 2×TY medium 100 μg/ml ampicillin in an incubator shaker until the cultures reached an $A_{600}$ of 0.8. The cells were induced with 1 mM IPTG at 30° C. with shaking for 16 h. The cells were harvested by centrifugation and washed with 20 mM potassium phosphate buffer for use in transformation assays. 2-(4-Carboxyphenyl)-6-nitrobenzothiazole 7a (49 μM) was incubated with the cells E. coli C43(DE3)pNbzAHabA (i.e. strain JS995) and HPLC analysis of the reaction mixture revealed a transformation rate for the parent compound of 0.9 nmoles $min^{-1}$ $mg^{-1}$ protein and the accumulation of one product (FIG. 1). LC/MS (+APCI) analysis of the product revealed a 287 m/z as expected of an aminophenol. The conversion efficiency was 100%. The transformation was scaled up to a 2 L bioreactor containing M9 medium (30° C.) supplemented with sorbitol (20 g/L), ampicillin (100 μg/L) and isopropylthio-β-D-galactoside (1 mM). Induced cells were added to the bioreactor ($A_{600}$=8.0) and 7a (5 mM) dissolved in $NH_4OH$ (2 N) at 65° C. was delivered repeatedly to the reactor. The disappearance of reactant and accumulation of product was monitored by HPLC. Over a 2 hour period, 200 mg of 7a was converted. The cells were removed by centrifugation and the product was precipitated by adjusting the pH of the supernatant to 2.7 with HCl. Green crystals were recovered by centrifugation. The crystals were dissolved in $NH_4OH$, filtered and recrystallized by lowering the pH to 2.7. The pelleted crystals were dried overnight under vacuum, washed with water and then acetone. The melting point was 326-328° C.

The proton NMR spectrum (270 MHz) of the purified compound in DMSO-$d_6$ showed that in the aromatic proton region, there were three singlet peaks at δ (ppm) 7.117, 7.309, and 8.012 at relative intensities of 1:1:4. The FT-IR (KBr) spectrum is consistent with the NMR data, indicating the presence of v(C=O) of carboxylic acid at 1692 $cm^{-1}$ and a strong, broad band centered ~3431 $cm^{-1}$ that is attributable to the hydroxyl-group vibrations of the carboxylic acid and the phenol moieties. The symmetrical and asymmetrical $NH_2$ stretches, typically detected as doublet at ~3400 and ~3500 $cm^{-1}$ respectively, are most likely hidden underneath the broad v(OH) band. Electron-impact mass spectroscopy gave a molecular ion with m/z=285.96 (100% relative abundance). Thus, all the available spectroscopic data confirm the structure of the product as 4-(6-amino-5-hydroxybenzothiazol-2) benzoic acid.

Having thus described exemplary embodiments of the present invention, it should be noted by those skilled in the art that the disclosures herein are exemplary only and that alternatives, adaptations and modifications may be made within the scope of the present invention.

We claim:
1. 2-(4-Carboxyphenyl)-6-nitrobenzothiazole having the chemical structure:

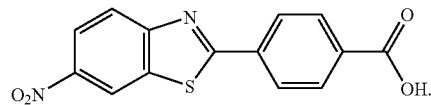

2. 4-(6-Amino-5-hydroxybenzothiazol-2-yl)benzoic acid having the chemical structure:

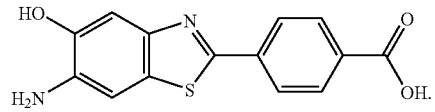

3. An enzymatic process for synthesizing the 4-(6-amino-5-hydroxybenzothiazol-2-yl)benzoic acid of claim 2, said process comprising the steps of:
   a.) providing a 2-(4-carboxyphenyl)-6-nitrobenzothiazole and a recombinant E. coli JS995 strain that expresses both nitroreductase and mutase activities;
   b) incubating said recombinant E. coli strain with said 2-(4-carboxyphenyl)-6-nitrobenzothiazole;
   c) converting said 2-(4-carboxyphenyl)-6-nitrobenzothiazole to said 4-(6-amino-5-hydroxybenzothiazol-2-yl) benzoic acid by said recombinant E. coli JS995 strain; and
   d) recovering a fraction containing said 4-(6-amino-5-hydroxybenzothiazol-2-yl)benzoic acid.

* * * * *